United States Patent [19]

Cummins

[11] Patent Number: 5,017,371

[45] Date of Patent: May 21, 1991

[54] METHOD FOR REDUCING SIDE EFFECTS OF CANCER THERAPY

[75] Inventor: Joseph M. Cummins, Amarillo, Tex.

[73] Assignee: Amarillo Cell Culture Company, Incorporated, Amarillo, Tex.

[21] Appl. No.: 141,621

[22] Filed: Jan. 6, 1988

[51] Int. Cl.$^5$ .............................................. A61K 37/66
[52] U.S. Cl. .................................... 424/85.6; 424/85.4; 424/85.7
[58] Field of Search ..................... 424/85.4, 85.5, 85.6, 424/85.7

[56] References Cited

U.S. PATENT DOCUMENTS

| | | |
|---|---|---|
| 3,536,809 | 10/1980 | Applezweig . |
| 3,906,092 | 9/1975 | Hilleman et al. . |
| 3,972,995 | 8/1976 | Tsuk et al. . |
| 4,053,582 | 10/1977 | Stickl . |
| 4,226,848 | 10/1980 | Nagai et al. . |
| 4,273,703 | 6/1981 | Osther et al. . |
| 4,276,282 | 6/1981 | Sugimoto et al. . |
| 4,460,574 | 7/1984 | Yabrov . |
| 4,462,985 | 7/1984 | Cummins, Jr. . |
| 4,497,795 | 5/1985 | Cummins . |
| 4,572,832 | 2/1986 | Kigasawa et al. . |
| 4,605,555 | 4/1988 | Sato et al. . |
| 4,649,075 | 3/1987 | Jost . |
| 4,675,184 | 6/1987 | Hasegawa et al. . |
| 4,746,508 | 5/1988 | Carey et al. . |
| 4,764,378 | 8/1988 | Keith et al. . |

FOREIGN PATENT DOCUMENTS

| | | |
|---|---|---|
| 4841285 | 4/1986 | Australia . |
| 0177342 | 4/1986 | European Pat. Off. . |

OTHER PUBLICATIONS

Goldstein, D. et al., Cancer Research, vol. 46, pp. 4315-4329, 1986.
"Alpha Interferon: A Look to the Future", Eric M. Bonnem, Investigational New Drugs 5, Suppl. 65-75 (1987), Nijhoff Publishers, Boston, pp. S65-S-75.
Rodder, H., Thumann, D., Thumann, E., Tierarztliche Umschau, vol. 34, No. 10, 1979, pp. 720-724 (summary).
Toneva, V., Bulletin de l'Office International des Epizooties, vol. 88, 1977, pp. 631-637 (Summary).
"In Vivo and Clinical Studies", Norman B. Finter & Robert K. Oldham, eds., Interferon, vol. 4, 1985, pp. 137, 148, 173, 218, 226, 284, 285, 330.
Chemical Abstracts, vol. 67, 1967, p. 7536 [80070u], Litvinov, A. N.
"Time and Dosage Dependence of Immunoenhancement by Murine Type II Interferon Preparations", Cellular Immunology, 40, 1978, pp. 285-293.
"Interferons and Their Actions", W. E. Stewart II and A. A. Gottlieb, eds., 1977, pp. 102-104.
"Antiviral Effect of Bacterially Produced Human Interferon (Hu-IFNA$_2$) Against Experimental Vaccinia Infection in Calves", Journal of Interferon Research, 5:129-136, 1985, Werenne, J., Broecke, C. V., Schwers, A., Goossens, A., Bugyaki, L., et al.
"Effect of Human Leukocyte A Interferon on Prevention of Infectious Bovine Rhinotracheitis Virus Infection of Cattle", Roney, C. S. et al., Am. J. Vet. Res., vol. 46, No. 6, Jun. 1985, pp. 1251-1255.
"Response of Feline Leukemia Virus-Induced Nonregenerative Anemia to Oral Administration of an Interferon-Containing Preparation", Feline Practice, vol. 12, No. 3, May-Jun. 1982, pp. 6-15, Tompkins, M. B. and Cummins, J. M.
"Interferon Enters the Fray", Farm Journal, Oct. 1985, pp. 12-13, Miller, B.
"Interferon as an Adjuvant for Hepatitis B Vaccinationin Non- and Low-Responder Populations", Grob, P. J. et al., Eur. J. Clin. Microbiol., Jun. 1984, vol. 3, No. 3, pp. 195-198.
"Protection of Calves Against Rhinovirus Infection by Nasal Secretion Interferon Induced by Infectious Bovine Rhinotracheitis Virus", American Journal of Veterinary Research, Cummins, J. M. and Rosenquist, B. D., Feb. 1980, vol. 41, No. 2, pp. 161-165.
"Bovine Respiratory Disease—A Symposium", R. W. Loan, ed., Texas A&M University Press, College Station, Tex. 1984, pp. 484-485.
"Activity of Exogenous Interferon in the Human Nasal Mucosa", Texas Reports on Biology and Medicine, vol. 35, 1977, Greenberg, S. B., Harmon, M. W. and Johnson, P. E., pp. 491-496.
"Inhibition of Respiratory Virus Infection by Locally Applied Interferon", Merigan, T. C., Hall, T. S., Reed, S. E., and Tyrrell, D. A., The Lancet, Mar. 17, 1973, pp. 563-567.
"Trials of Interferon in Respiratory Infections of Man", Tyrrell, D. A. J., Texas Reports on Biology and Medicine, vol. 35, 1977, pp. 486-490.
"Bacteria-Derived Human Leukocyte Interferons After in Vitro Humoral and Cellular Immune Responses", Cellular Immunology, 82, 1983, pp. 269-281, by Shalaby, M. R. and Weck, P. K.
"Clinical and Laboratory Investigations on Man: Systemic Administration of Potent Interferon to Man", J. Natl. Cancer Inst., 51: 733-742, 1973, by Strander, H., Cantell, K., Carlstrom, G. and Jakobsson, P. A.
"Application of Human Leukocyte Interferon in Severe Cases of Virus B Hepatitis", Vlatkovic, R., et al., Proc. Symposium on Interferon 1979, Yugoslav Academy of Sciences and Arts, Zagreb, pp. 173-183.

(List continued on next page.)

Primary Examiner—Howard E. Schain
Assistant Examiner—Choon P. Koh
Attorney, Agent, or Firm—Barnes & Thornburg

[57] ABSTRACT

Low doses of interferon contacted with the oral and pharyngeal mucosa of a patient in conjunction with administration of radiation therapy or chemotherapy reduces the toxic side effects associated with administration of said cancer therapy.

19 Claims, No Drawings

OTHER PUBLICATIONS

"Effect of Interferon on Vaccination in Volunteers", *The Lancet*, Apr. 28, 1962, pp. 873–875 (Report to Medical Research Council from the Scientific Committee on Interfron).

"Induction of Ocular Resistance to Vaccinia Virus by Typhoid Vaccine: Role of Interferon", Oh, J. O., and Yoneda, C., *The Journal of Immunology*, vol. 102, No. 1, 1969, pp. 145–154.

"Clinical Trials with Exogenous Interferon: Summary of a Meeting", *The Journal of Infections Diseases*, vol. 139, No. 1, Jan. 1979, pp. 109–123.

"Some Results and Prospects in the Study of Endogenous and Exogenous Interferon", *The Interferson, An International Symposium*, Soloviev, V. D., Geo. Rita, ed., Academic Press, 1968, pp. 233–243.

"Influenza and Interferon Research in the Soviet Union—Jan. 1973", *The Journal of Infectitous Diseases*, vol. 128, No. 2, Aug. 1973, pp. 261–264.

"The Results of Controlled Observations on the Prophylaxis of Influenza with Interferon", Solov'ev, V. D., *World Health Organization*, 1949, 41, 683–688.

"Children's Respiratory Viral Diseases Treated with Interferon Aerosol", Jia-xiong, D. et al., *Chinese Medical Journal*, 100(2): 162–166, 1987.

*Essential Clinical Virology*, R. G. Sommerville, Blackwell Scientific Publications, pp. 154–157.

"Comparative Intranasal Pharmacokinetics of Interferon Using Two Spray Systems", Davies, H. W. et al., *J. Interferon Research*, 1983, pp. 443–449.

"The Common Cold Control?", Couch, R. B., *The Journal of Infectitious Diseases*, vol. 150, No. 2, Aug. 1984, pp. 167–173.

*Principles and Practice of Infectious Diseases*, 2nd. ed., Mandell, G. L., Douglas, R. G. Jr., Bennett, J. E. eds., A Wiley Medical publication, pp. 85–96, 863, 968.

*Antiviral Agents and Viral Diseases of Man*, edited by G. J. Galasso, T. C. Merigan, R. A. Buchanan, Raven Press, New York, 1979, pp. 407–408, 430–431.

*Antiviral Agents and Viral Diseases of Man*, edited by G. J. Galasso, T. C. Merigan, R. A. Buchanan, Raven Press, New York, 1984, pp. 145–178, 344–345.

"Interferon Perspective", Information on Interferon provided in 1981 by the International Preventative Medicine Foundation, Melbourne, Fla., Ronald Jones, Vice President.

American Interhealth, Melbourne Beach, Florida, production information.

Biovet International, Inc., Canine and Feline Interferons, 1981 product description and label.

"Agriferon®-C", Immuno Modulators Laboratories, Inc., Stafford, Texas, Lymphokine Preparation for Prophylactic Treatment of Infectious Bovine Rhinotracheitis Virus Associated with Shipping Fever—for cattle use in Texas only, product brochure.

"Agriferon®-C", A Bold New Approach to Managing Shipping Fever in Cattle, Immuno Modulators Laboratories, Inc., Stafford, Texas, product advertisement.

"Equiferon" A Totally New Approach to Viral Respiratory Infection in Horses, Immuno Modulator Laboratories, Inc., Stafford, Texas, 1985, product advertisement.

"Pet Interferon Alpha", Amarillo Cell Culture Company, Inc., Amarillo, Texas, Lymphokine Preparation for Treatment of Feline Leukemia Virus and Canine Parvovirus Diseases, product brochure.

Texas Department of Health application for license, Amarillo Cell Culture Company, Inc., for human interferon alpha, (Alpha Interferon) as Pet Interferon, May 6, 1985.

"Circulating Interferon in Rabbits After Administration of Human Interferon by Different Routes", Cantel, K. and Ryhala, L., *Journal of General Virology*, (1973), 20, pp. 97–104.

"Pharmacokinetics of Recombinant Alpha A Interferon Following IV Infusion and Bolus, IM, and PO Administrations to African Green Monkeys", Wills, R. J., Spiegel, H. E., and Soikel, K. F., *Journal of Interferon Research*, vol. 4, No. 3, 1984, pp. 399–409.

"Pharmacokinetics of Recombinant Leukocyte A Interferon Following Various Routes and Modes of Administration to the Dog", Gibson, D. M. et al., *Journal of Interferon Research*, 5:403–408 (1985).

"Stimulation of Humoral Immunity by Interferon", *III Mediterranean Congress of Chemotherapy*, Smerdel, S., et al., Sep. 21–24, 1982 presentation, vol. 2, p. 132, Oct. 1983.

"Interferon Preparations as Modifiers of Immune Responses", Braun, W., Levy, H. C., *Proc. Soc. Exp. Biol. Med.*, vol. 141, pp. 769–773, 1972.

"Interferon and the Immune System: A Review (Limited to Alpha and Beta Interferons)", De Maeyer, Edward, *The Biology of the Interferon System*, pp. 203–209, Elsevier/North-Holland Biomedical Press, 1981.

"Effect of Virus-Induced Interferon on The Antibody Response of Suckling and Adult Mice", Vignauz, F., et al., *Eur. J. Immunol.*, vol. 10, pp. 767–772, 1980.

"The Clinical Use of Human Leukocyte Interferon in Viral Infections", Ikic, D., et al., *International Journal of Clinical Pharmacology, Therapy and Toxicology*, vol. 19, No. 11, pp. 498–505, 1981.

"Primjena Humanog Leukocitnog Interferona U Male Djece Sa Gingivostomatitisom", Salaj-Rakic, T., et al., *Proceedings—Yougoslav-Pediatric Congress*, Sarayevo, 1979, p.730.

"Colorectal Administration of Human Interferon-Alpha", Bocci, et al., *International Journal of Pharmaceutics*, vol. 24, pp. 109–114, 1985.

"Interferon Administered Orally: Protection of Neonatal Mice From Lethal Virus Challenge", Schafer, T., et al., *Science*, Jun. 23, 1972, vol. 176, pp. 1326–1327.

"Erste Erfahrungen bei der Behandlung von Virusbedington Kalberdurchfallen mit Gentechnisch Erzeugtem Interferon", Hofmann, V. W., et al., *Dtsch. Tierarztl. Wschr.*, vol. 92, pp. 278–280.

"Differential Modification of Morphine and Methadone Dependence by Interferon Alpha", Dougherty, P. M., et al., *Neuropharmacology*, vol. 26, No. 11, pp. 1595–1600, 1987.

METHOD FOR REDUCING SIDE EFFECTS OF CANCER THERAPY

BACKGROUND AND SUMMARY OF THE INVENTION

This invention relates to a method for reducing the toxic side effects of cancer therapy. More particularly this invention relates to the use of interferon administered in a form adapted to promote contact with the inside of a patient's mouth and pharynx to reduce the undesirable side effects resulting from the administration of radiotherapy and chemotherapeutic agents during the treatment of cancer.

Treatment of cancer has, over the last twenty years, been the focus of a significant research and development effort. Many approaches to cancer therapy have been investigated. As a practical matter, cancer therapy can involve use of multiple treatment methods including surgical excision, radiation therapy (radiotherapy), chemotherapy, and bone marrow transplantation (for treatment in patients with some types of hematological malignancies, particularly acute myelocytic leukemia). The specific protocol utilized to treat a given malignancy, depends on the nature, location and type of malignancy being treated. Surgical excision is the preferred method for treatment of primary circumscribed tumors. Often, however, surgical excision is combined with radiation therapy and/or chemotherapy to complete the treatment protocol. In instances where the malignancy is not localized or where its location lowers the probability of successful removal or excision by surgical techniques, chemotherapy and radiation therapy are often used in combination.

Chemotherapy has been shown to produce long term remissions in patients with some types of cancer, including Hodgkin's Disease, acute lymphocytic and myelogenous leukemia, testicular cancer and non-Hodgkin's lymphoma. In other types of cancer, chemotherapy has been used successfully to decrease the size of large primary tumors prior to surgery. Chemotherapy often involves the use of combinations of chemotherapeutic agents. New protocols (programs for combination drug treatment) are being developed and tested continuously by the medical research community.

Anti-tumor agents are drugs which, in addition to killing tumor cells, can and do damage normal tissue. Even with the extensive research that has been conducted to define dosage levels and scheduling of drug administration, chemotherapy often results in unpleasant and possibly dangerous side effects due to drug toxicity. Radiation therapy produces many of the same problems. Most common of such side effects are nausea and vomiting, alopecia (hair loss), and bone marrow depression. Such side effects are usually, but not always, reversible. Some anti-cancer drugs may permanently damage the nervous system, heart, lungs, liver, kidneys, gonads or other organs. Some chemotherapeutic agents are themselves carcinogenic. Patients undergoing radiotherapy or chemotherapy must also take precautions to avoid what can be life threatening infections in their therapy-induced immuno-suppressed condition.

Treatments have been developed to counteract the side effects of cancer radiotherapy and chemotherapy. For example, drugs can be administered to provide some relief from nausea, antibiotics can be administered to help fight infection, and transfusions can be administered to increase blood cell and platelet counts if necessary.

In accordance with this invention it has been found that interferon administered in conjunction with cancer therapy is effective to reduce the undesirable side effects of cancer therapy. The effective route of administration is by contact of interferon in relatively low dosages with the patient's oral and pharyngeal mucosa. It is necessary that the interferon be administered in a form adapted to promote contact with the inside of the patient's mouth and throat in amounts effective to reduce the toxic side effects of cancer therapy, including chemotherapy and radiation therapy.

DETAILED DESCRIPTION OF THE INVENTION

"Interferon" is a term generically comprehending a group of vertebrate glycoproteins and proteins which are known to have various biological activities, such as antiviral, antiproliferative and immunomodulatory activity, at least in the species of the animal in which such substances are derived. The following definition of "interferon" has been accepted by an international committee assembled to devise a system for the orderly nomenclature of interferons: "To qualify as an interferon a factor must be a protein which exerts virus non-specific, antiviral activity at least in homologous cells through cellular metabolic process involving synthesis of both RNA and protein." *Journal of Interferon Research*, 1, pp. vi (1980). "Interferon" as used herein in describing the present invention shall be deemed to have that definition and shall contemplate proteins, including glycoproteins, regardless of their source or method of preparation or isolation.

Interferons have generally been named in terms of the species of animal cells producing the substance (e.g., human, murine, bovine, etc.), the type of cell involved (e.g., leukocyte, lymphoblastoid, fibroblast) and, occasionally, the type of inducing material responsible for the interferon production (e.g., virus, immune). Interferon has been loosely classified by some researchers according to the induction mode as either Type I or Type II, with the former classification comprehending viral and nucleic acid induced interferon, and the latter class including the material produced as a lymphokine through induction by antigens and mitogens. More recently, the international committee devised an orderly nomenclature system for interferon and has classified interferons into types on the basis of antigenic specificities. In this newer classification, the designations alpha ($\alpha$), beta ($\beta$) and gamma ($\gamma$) have been used to correspond to previous designations of leukocyte, fibroblast and Type II (immune) interferons, respectively. Alpha and beta interferons are usually acid-stable and correspond to what have been called Type I interferons. Gamma interferons are usually acid-labile and correspond to what have been called Type II interferons. The international committee's nomenclature recommendations apply only to human and murine interferons. *Journal of Interferon Research*, 1, pp. vi (1980).

The use of interferon for the treatment of disease in man and animals has been the subject of intense ongoing research efforts in many laboratories, both in industry and in educational institutions around the world. In some of the earliest research activities interferon was shown to have antiviral properties and the most successful clinical therapeutical applications to date have been in the treatment of virus-related disease states. More recently it has been found that exogenous interferon is effective for the regression or remission of some metastatic disease states. An overview of recent clinical trials of interferon as an antiviral and antiproliferative therapeutic agent is contained in *Interferon; In Vivo and Clinical Studies*, vol. 4, eds. N. B. Finter and R. K. Oldham, Academic Press, N.Y., 1985. The literature is replete with reports of research and development efforts directed to defining activities and potential therapeutic uses of interferon. Most of the reports described activities of interferon in vitro or its effects in vivo following parenteral, particularly intramuscular and intradermal administration. There have been some reports of successful topical and intranasal usages. It has seldom been administered intravenously because of substantial adverse effects attributable to "contaminants" in crude and even highly purified isolates. While the advent of recombinant DNA technology has allowed production of pure interferon species, intravenous administration of such pure compositions are not without adverse effects. It is noted here that the Food and Drug Administration has approved the use of alpha-interferon administered parenterally in high doses for the treatment of human hairy cell leukemia.

Before Applicant's first report of a successful oral administration of interferon in his now issued U.S. Pat. No. 4,462,985, there was no recognition in the art of the potential offered by oral administration of interferon. The generally held belief was that interferon could not survive the digestive conditions of the upper alimentary canal. Since Applicant's first disclosure of the immunotherapeutic benefit achieved via oral administration of interferon, he has continued to investigate the efficacy of orally administered interferon. In U.S. Pat. No. 4,497,795, issued Feb. 5 1985, Applicant described and claimed the use of interferon administered orally or via intravenous administration to stimulate appetite and feed efficiency of animal species. More recently Applicant has described in now pending U.S. Pat. applications, the use of interferon at dosages less than about 5 IU/lb of body weight for increasing feed efficiency and food utilization in warm-blooded vertebrates, for preventing and treating shipping fever, and for enhancing vaccine efficiency. Since those earlier applications, Applicant has discovered that the efficacy of orally administered interferon is realized only if it is administered in a form which promotes contact of the interferon dosage with the mucosal lining (possibly macrophages and lymphatics) of the mouth and throat. That discovery in part formed the basis of Applicant's U.S. Pat. application Ser. No. 927,834, filed Nov. 6, 1986, titled "Treatment of Immuno-Resistant Disease".

Human alpha-interferon has been marketed under the trademark Agriferon ® by Immunomodulator Laboratories, Inc. ("IML") of Stafford, Tex., for veterinary use in Tex. since Feb. 1985. The product is sold for oral administration to cattle to promote growth and feed efficiency and to prevent or treat viral respiratory infections. IML began selling an alpha-interferon product for horses in 1986. Both products are sold under a license of U.S. Pat. No. 4,462,985. The Amarillo Cell Culture Company, Inc. of Amarillo, Tex. markets human-alpha interferon for use in dogs and cats.

The clinical agent of choice for use in the present invention is human leukocyte interferon (human alpha-interferon), mass produced by procedures involving collection and purification of quantities of human buffycoat leukocytes, induction of interferon production with virus, and isolation from culture media. (See "Preparation of Human Alpha-Interferon" below.) Also acceptable for use in accordance which the present invention are human alpha-interferon products produced by recombinant DNA technology and now commercially available from Schering-Plough (as Intron ®) and Hoffmann-La Roche (as Roferon ®) and approved by the FDA for treatment (parenterally) of hairy cell leukemia of man. Gamma-interferon is also available by recombinant technology and is presently undergoing clinical trials by Genentech, Inc. and others. Fibroblast interferon (beta-interferon) can be prepared in accordance with Example 1 in Applicant's U.S. Pat. No. 4,462,985, issued Jul. 31, 1984, the disclosure of which is hereby expressly incorporated by reference.

Interferon of human and murine origins has been quantified in the art in terms of International Units ("IU"). Interferons of other than human or murine origin can be used in accordance with this invention, and to the extent that application of "International Units" to those interferons may be outside presently accepted practices for specification of quantities of said interferons, it shall be understood that amounts of non-human interferons having the same efficacy as the quantities (IU's) of human interferon specified in accordance with this description is within the scope of the present invention.

In accordance with one preferred embodiment of the present invention, the toxic side effects resulting from the administration of chemotherapeutic agents in a patient receiving chemotherapy for treatment of cancer are reduced by a method comprising contacting the oral and pharyngeal mucosa of said patient with interferon in an amount effective to reduce said side effects.

Exemplary of chemotherapeutic agents which are known to produce undesirable side effects in most patients undergoing chemotherapy for treatment of cancer include adrimycin, bleomycin, carmustine, cysplatin, cyclophosphamide, cytarabine (ARA-C), dacarbozine, dactinomycin, etoposide, 5-fluorouracil, hydroxyurea, lumustine, mercaptopurine, methotrexate, mytomicin, prednisone, procarbazine hydrochloride, vinblastine and vincristine. Such oncolytic agents are typically used in combination with others listed or other art-recognized chemotherapeutic agents for treatment of neoplastic disease and are all recognized to have contraindications of both acute toxicity and delayed toxicity. Acute toxicity is manifested in side effects such as nausea and vomiting, fever, chills, abdominal pain, hyperglycemia, seizures, diarrhea, hypotension, ventricular arrhythmia, anaphylaxis and localized phlebitis. Delayed toxicity can appear as bone marrow depression and concomitant immuno-suppression, renal damage, thrombosis, alopecia (hair loss), cataracts, liver damage, sterility, hemorrhagic cystitis, pulmonary edema, conjunctivitis, impotence, stomatitis, dermatitis, neurological defects, hypokalemia and hypocalcemia, and the like. Cutaneous reactions, hyperpigmentation and ocular toxicity have been reported with virtually all non-hormonal anti-cancer drugs.

Interferon administered in accordance with this invention has been observed to reduce the side effects resulting from administration of chemotherapeutic agents. The interferon can be derived from human cells or animal cells, or from microorganisms produced by recombinant engineering techniques to contain one or more functioning genes for human or animal interferon. Proteins having activities similar to natural occurring interferons but with modified amino acid sequences (semi-synthetic interferons) are also contemplated as useful in accordance with this invention.

Interferon is administered to the patient in a dosage form adapted to promote contact with the administered interferon with the patient's oral and pharyngeal mucosa. Thus, the dosage form is preferably in the form of an interferon-containing solution or syrup to be administered and used by the patient in a manner which promotes contact of the interferon component with the oral and pharyngeal mucosa. Alternatively, the interferon can be formulated into a solid dosage from which dissolves when held in the patient's mouth in contact with saliva to release effective amounts of interferon for contact with the oral and pharyngeal mucosa. Other solid or liquid vehicles adapted to accomplish that important function in accordance with this invention can be employed.

Effective dosage levels of interferon for use in accordance with this invention are low compared to levels of alpha-interferon administered parenterally for treatment of some forms of cancer. Thus, while art-recognized dosage ranges for parenteral administration of alpha-interferon for the treatment of human hairy cell leukemia are in excess of $10^6$ IU per dose, effective doses of interferon in accordance with the present invention are typically less than 1500 IU per dose. Preferably interferon is administered in accordance with this invention at a dosage level of less than 10 IU/lb of patient weight per day and more preferably about 0.1 to about 5.0 IU/lb of patient weight per day. A most preferred dosage is about 1 to about 1.5 IU human alpha-interferon per pound of patient weight per day. Equally effective amounts of human beta-interferon or alpha (or beta) interferon of non-human species origin can be used.

Treatment of the patient in accordance with this invention is ideally, although not necessarily, initiated in advance of administration of the chemotherapeutic agents or radiotherapy. Preferably interferon is administered at least one day and better, at least a week prior to beginning cancer therapy. Patient treatment with interferon in accordance with this invention is preferably continued throughout the patient's cancer treatment program.

Daily dosage of interferon can be administered as a single dose or, it can be divided and administered as a multiple-dose daily regimen. A staggered regimen, for example 1 to 3 days treatment per week, can be used as an alternative to continuous daily treatment.

Interferon can be administered in accordance with this invention in either a liquid (solution) or in solid dosage form. Thus interferon can be administered in a buffered aqueous solution typically containing a stabilizing amount (1–5% by weight) of albumin or blood serum. Exemplary of a buffered solution suitable as a carrier of interferon administered in accordance with this invention is a phosphate buffered saline solution prepared as follows: A concentrated (20x) solution of phosphate buffered saline (PBS) was prepared by dissolving the following reagents in sufficient water to make 1000 ml of solution: sodium chloride, 160 g.; potassium chloride 4.0 g.; sodium hydrogen phosphate 23 g.; potassium dihydrogen phosphate 4.0 g.; and optionally, phenol red powder 0.4q. The solution is sterilized by autoclaving at 15 lbs. pressure for 15 minutes and then diluted with additional water to a single strength concentration prior to use.

Alternatively the interferon utilized in accordance with this invention can be formulated into flavored or unflavored solutions or syrups, for example, using a buffered aqueous solution of interferon as a base with added caloric or non-caloric sweeteners, flavors and pharmaceutically acceptable excipients.

A solid dosage form, such as a lozenge adapted to be dissolved upon contact with saliva in the mouth, with or without the assistance of chewing is an equally acceptable means for administering interferon in accordance with this invention. Such a unitary dosage form is preferably formulated to release about 1 to about 1500 IU of interferon upon dissolution in the mouth for contact with the oral and pharyngeal mucosa. Thus a unitary dosage form of interferon in accordance with this invention can be prepared by art-recognized techniques for forming compressed tablets such as chewable vitamins. Similarly, interferon can be incorporated, for example, into a starch-based gel formulation which will dissolve and release interferon for contact with the oral mucosa when held in the mouth. Solid unitary dosage forms of interferon for use in accordance with this present invention can be prepared utilizing art-recognized dose formulation techniques. The pH of such formulations can range from about 4 to about 8.5.

Preparation of Human Alpha-Interferon

Human alpha-interferon can be prepared through the following procedure, commonly referred to as the Cantell procedure. The process begins with packs of human leukocytes, obtained in this case from the Gulf Coast Regional Blood Center, Houston, Tex. The buffy coats in these packs are pooled into centrifuge bottles, and then are diluted with 0.83% ammonium chloride. The mixture is incubated for 15 minutes with intermittent shaking, and is then centrifuged for 20 minutes at 2000 rpm. The supernatant is discarded, and the cell pellets are resuspended with a minimal volume of sterile PBS. The mixture is then diluted with ammonium chloride and centrifuged. The supernatant is again discarded, and the remaining cell pellets are resuspended with a minimal volume of a tissue culture medium such as Minimal Essential Medium (MEM), available from KC Biological. The cell concentration is determined with a Coulter counter.

Interferon induction takes place in glass or plastic bottles. The induction medium contains MEM, 75 mM Hepes (available from Calbiochem), 75 mM Tricine (available from Sigma Chemical Co.), human agamma serum (18 mg/ml), and gentamycin sulfate (from M.A. Bioproducts; 50 mcg/ml). The cells are added to the induction vessels at a final concentration of about 5 to 10 million cells per milliliter. The induction vessel is incubated in a 37° C. water bath, and alpha-interferon is added as a primer.

After two hours, Sendai virus is added to the induction mixture. This causes alpha interferon to be produced in the supernatant by the leukocytes. After a 12–18 hour incubation time, the induction mixture is centrifuged. The cells are discarded, and the supernatant is then purified.

The crude interferon is chilled to 10° C. or below in an ice bath. Five molar potassium thiocyanate is added to obtain a final concentration of 0.5 M. This solution is stirred for 15 minutes, and then its pH is lowered to 3.3 by adding hydrochloric acid. The mixture is then centrifuged at 2800 rpm for 30 minutes, and the supernatant is discarded.

The pellets are then resuspended in 95% ethanol and are stirred for 15 minutes. This suspension is centrifuged at 2800 rpm for 20 minutes, and the pellets are discarded. The pH of the supernatant is then adjusted to 5.8 with sodium hydroxide. The mixture is stirred for 10 minutes, and then centrifuged at 2800 rpm for 20 minutes. The pellets are discarded. The pH of the supernatant is then adjusted to 8 with sodium hydroxide. This solution is stirred for 10 minutes, followed by centrifugation at 2800 rpm for 20 minutes. The supernatant is discarded, and the pellets are resuspended with 0.5 M potassium thiocyanate in a 0.1 M sodium phosphate buffer. This suspension is stirred at 4° C.

Next, the suspension is centrifuged at 2800 rpm for 20 minutes, and the pellets are discarded. The pH of the supernatant is adjusted to 5.3 with hydrochloric acid. After stirring for 10 minutes and centrifugation, the pH of the supernatant is adjusted to 2.8 with hydrochloric acid, followed by further stirring for 20 minutes. This mixture is centrifuged at 2800 rpm, and the resulting pellet is purified human alpha-interferon.

The pellet is resuspended with 0.5 M potassium thiocyanate in 0.1 M sodium phosphate buffer, having a pH of 8.0. It is then dialyzed against PBS at 4° C., with two changes of PBS. This mixture is then centrifuged and the precipitate is discarded. The remaining purified alpha interferon is sterilized by filtration through a 0.2 micron filter. A human alpha-interferon has been produced in accordance with this procedure by Immuno Modulators Laboratories, Inc., Stafford, Tex., and sold under the trademark Agriferon ® for use in cattle and Equiferon ® for use in horses.

Other Procedures known to those skilled in the art are available for making interferons, such as human alpha-interferon and human gamma-interferon. For example, U.S. Pat. Nos. 4,376,821 and 4,460,685 disclose methods of making human gamma-interferon. A method of making bovine fibroblast (beta) interferon is disclosed in applicant's U.S. Pat. No. 4,462,985.

EXAMPLE 1

A 40-year old, 150 pound male patient (R-1) suffering from an adenocarcinoma underwent surgery to remove a major portion of one lung and proximal lymph glands. He was subjected postoperatively to maximum allowed dose of Cobalt-60 radiation therapy. Routine postoPerative fluroscopic examination 5 months after surgery revealed new tumor growth in lung tissue. Patient R-1, having been informed by his oncologist of a poor prognosis, sought other therapeutic methods for treatment of his cancer.

R-1 initiated a carefully maintained dietary regimen which in general terms was a vitamin and herbal supplemented, low fat diet. R-1's regimen further included a daily dosage of about 150 IU of human alpha-interferon (Cantell) in phosphate buffered saline (150 IU/ml) taken into his mouth for contact with his oral and pharyngeal mucosa. The solution was administered using a 3-ml syringe to direct the interferon solution onto the mucosa lining the mouth. R-1 used his tongue to manipulate the interferon-containing solution in his mouth to maximize contact with the oral and pharyngeal mucosa. Within one week of the initial low dosage of interferon, R-1 noted a significant improvement in a conjestive respiratory condition that had troubled him during and subsequent to radiation therapy.

R-1 continued his daily self-administered dosages of interferon solution up until a time immediately proceeding his participation in a study of a new, experimental oncolytic agent at a major midwestern medical center. The study involved treatment with an unidentified experimental drug in patients receiving, at the same time, other known oncolytic agents. R-1 received treatments with the experimental drug in conjunction with the administration of 5-flurouracil. R-1 experienced markedly less toxicity effects (nausea and intestinal discomfort) than did other patients receiving the same therapy. R-1 was nauseous for no more than one hour following his completion of intravenous administration of the drugs under study. He was able to undergo therapy on an outpatient basis, and he reports that he was able to work at home between his daily visits to the medical center for chemotherapy. His oncologist commented both on R-1's ability to withstand the experimental therapy with markedly reduced nausea compared to other patients in the study and on the results of R-1's blood analysis. R-1's white cell counts, while being reduced as expected bY the chemotherapy, rebounded to normal levels much more rapidly than those in other patients in the study.

R-1 resumed his dosages of interferon as described above following participation in the first study. R-1 participated later in a second experimental study conducted to determine efficacy of a chemotherapeutic agent reportedly consisting of a chemotherapeutic agent coupled to monoclonal antibodies. Again R-1's oncologist noted and commented on R-1's much reduced pain, less nausea, and fewer symptoms attributed to the chemotherapy toxicity compared to those symptoms reported by other patients receiving the same experimental therapy.

EXAMPLE 2

A 6-year old male (N-1) suffering from acute myelogenous leukemia was treated to remission over a 3-4 month period using a chemotherapeutic regimen consisting of cytosine arabinoside (Ara-C), daunomycin, VP-16 (etoposide), 6-thioguanine and dexamethasone in the induction phase of treatment. During that induction phase N-1 experienced all of the characteristic side effects of chemotherapy including hair loss, nausea and vomiting, and bone marrow depression. Once N-1's leukemia was in remission he initiated a vitamin supplemented dietary regimen which included specifically daily amounts of vitamin C (1000 mg), Vitamin E (400 IU) and selenium supplement (50 mcg). N-1's weight is about 50 pounds.

Following the induction phase of N-1's treatment program, the second phase, the consolidation phase, of chemotherapy was initiated. The consolidation phase consists of several courses of cyclic chemotherapy combined with intrathecal drug administration to prevent leukemia of the central nervous system. In Course 1 of the consolidation phase, N-1 was given two treatments, 7 days apart, each consisting of four high doses of Ara-C given twelve hours apart followed by L-asparaginose. N-1 experienced the expected toxic effects of such therapy, including nausea, vomiting and bone marrow depression. Course 2 of the consolidation phase consists of 1 monthly regimen of 6-thioguanine orally for 28 days, vincristine sulfate i.v. for one day; Ara-C, 5-azacytidine and cyclophosphamide i.v. for four days. During the last four days of the first monthly regimen (i.v. administration phase), N-1 was very sick; he experienced significant nausea and vomiting on each day of i.v. drug administration.

Following that first phase of the second course of consolidation, N-1 began contacting his oral and pharyngeal mucosa daily with about 100 IU of human-alpha interferon (Cantell) administered in about 1 ml of a solution in sterile phosphate buffered saline. The solution was self-administered daily from a syringe from which it was discharged against the lining of the mouth and moved with the tongue to maximize contact with the oral and pharyngeal mucosa. During the i.v. administration phase of the second month of the second course of consolidation, N-1 experienced nausea and vomiting only on the first day of i.v./intrathecal drug administration. N-1 was able to eat regularly and play at home on each subsequent day of i.v.-chemotherapy.

N-1's oncologist has commented on N-1's high energy level, his lack of hair loss and less nausea and the rapid recovery of his white cell counts following chemotherapy compared to other patients at his age and stage of chemotherapy.

EXAMPLE 3

A 38-year old, 160 pound male patient (F-1) was diagnosed as positive for Kaposi's Sarcoma (KS) in Oct. 1986. F-1 was initially treated with vincristine, vinblastine and etopiside. Later F-1 was treated with vincristine (0.5 mg), vinblastine (2 mg), and bleomycin (5 units). Toxicity from therapy included painful oral ulceration, loss of appetite, nausea, and fatigue. F-1 added to his regimen a biweekly daily dosage of about 150 IU of human alpha-interferon (Cantell) in phosphate buffered saline (150 IU/ml) taken into his mouth for contact with his oral and pharyngeal mucosa. The solution was administered using a 3-ml syringe to direct the interferon solution onto the mouth. Within one week of the initial low dosage of interferon, F-1 noted a significant reduction of oral ulcers, improvement of appetite, weight gain, and an improved energy level compared to the toxicity which had troubled him during and subsequent to his therapy.

F-1 continued his intermittent self-administered dosages of human interferon solution up until a time he switched to bovine alpha-interferon (obtained from cattle nasal secretions). Bovine alpha-interferon relieved the toxicity of his weekly chemotherapy even more completely than human alpha-interferon. The combination of interferon and chemotherapy has resulted in complete remission of KS.

What is claimed:

1. A method for reducing side effects resulting from the administration of cancer therapy utilizing chemotherapeutic agents or radiation therapy in a patient receiving such therapy for treatment of cancer, said method comprising contacting the oral and pharyngeal mucosa of said patient with alpha-interferon or beta-interferon in an amount effective to reduce said side effects.

2. The method of claim 1 wherein the interferon is human alpha-interferon.

3. The method of claim 1 wherein the interferon is interferon of a non-human species or interferon produced by recombinant DNA technology.

4. The method of claim 1 wherein the patient is receiving chemotherapy.

5. The method of claim 4 wherein the interferon is human interferon.

6. The method of claim 4 wherein the interferon is administered daily during chemotherapy.

7. The method of claim 6 wherein the amount of interferon is about 0.1 to about 5 IU of interferon per pound of patient weight/per day.

8. The method of claim 1 wherein the amount of interferon is about 0.1 to about 5 IU of interferon per pound of patient weight per day.

9. The method of claim 8 wherein the interferon is alpha-interferon administered daily during cancer therapy.

10. The method of claim 9 wherein the interferon is administered daily beginning at least one day prior to initiation of chemotherapy.

11. The method of claim 1 wherein the interferon is administered in a dosage form adapted to be held in the patient's mouth for a period of time to maximize contact of the interferon with the oral and pharyngeal mucosa of said patient.

12. The method of claim 1 wherein the interferon is administered in the form of an interferon-containing solution.

13. The method of claim 1 wherein the interferon is administered in the form of a lozenge.

14. Method for treating a cancer patient to reduce the undesirable side effects of cancer chemotherapeutic agents, said method comprising the step of contacting the oral and pharyngeal mucosa of said patient with alpha-interferon or beta-interferon in an amount effective to reduce said side effects.

15. The method of claim 14 wherein about 0.1 to about 5 IU of interferon per pound of patient body weight is administered daily beginning at least one day prior to initiation of chemotherapy.

16. Method for reducing radiation-induced side effects in a patient undergoing radiation therapy for the treatment of cancer, said method comprising the step of contacting the oral and pharyngeal mucosa of said patient with interferon in an amount effective to reduce said side effects.

17. The method of claim 16 wherein about 0.1 to about 5 IU of interferon per pound of patient body weight is administered daily beginning at least one day prior to initiation of chemotherapy.

18. The method of claim 16 wherein the interferon is human alpha-interferon.

19. The method of claim 16 wherein the interferon is interferon produced by recombinant DNA technology.

* * * * *